United States Patent [19]
Steer et al.

[11] Patent Number: 6,095,996
[45] Date of Patent: Aug. 1, 2000

[54] ADHESIVE COMPOSITION OR STRUCTURE

[75] Inventors: Graham E. Steer, London; John A. Gent, Hampshire; Donald J. Highgate, Bucks, all of United Kingdom

[73] Assignee: Bristol-Myers Squibb Company, New York, N.Y.

[21] Appl. No.: 09/086,368

[22] Filed: May 28, 1998

[30] Foreign Application Priority Data

May 30, 1997 [GB] United Kingdom .................... 9711207

[51] Int. Cl.[7] ...................................................... A61F 13/00
[52] U.S. Cl. ................ 602/52; 428/355 R; 428/355 AC
[58] Field of Search .................................. 602/52, 41, 56; 428/40.1, 355 R, 355 AC

[56] References Cited

U.S. PATENT DOCUMENTS 5,571,080  11/1996  Jensen ........................................ 602/56

*Primary Examiner*—John G. Weiss
*Assistant Examiner*—K. Hart

*Attorney, Agent, or Firm*—Stuart E. Krieger

[57] ABSTRACT

An adhesive composition or structure is proposed for use in skin application, e.g. drug delivery wound care, or for attaching devices to collect body waste to the wearer. The composition comprises (a) a polymer or mixture of polymers which act as a pressure-sensitive adhesive present in an amount 20–60 parts by weight of the adhesive composition; and (b) a water-swellable polymer present in an amount 20–80 parts by weight of the adhesive composition. The polymer is one which will absorb from 50 to 500 grams of pure water per 100 grams of water-swellable polymer.

Additionally there may be present up to 30 parts by weight (of the adhesive composition) of a water-soluble polymer.

The water-swellable polymer may be provided as a coating on non-water-soluble and non-water-swellable fibers which limit swelling of the coating to be radial of the fibers. By arranging or aligning the fibers, the direction of swelling of the composition or structure can be controlled. An adhesive ostomy pad is described which expands substantially in only one direction to avoid blocking the stoma aperture.

7 Claims, 3 Drawing Sheets

ADHESIVE COMPOSITION OR STRUCTURE

BACKGROUND OF THE INVENTION

This invention relates to an adhesive composition.

Such compositions may be used for drug delivery, wound care or to attach appliances or devices to human skin. One example of a protective dressing is described in U.K. Patent No. 1,088,992. Since the publication of that patent, many adhesive compositions for these purposes have been proposed.

G. D. Searle & Co. of Illinois proposed in U.S. Pat. No. 4,296,745 (1981) an adhesive surgical dressing which comprises a backing material provided on one side with a composition comprising per 100 parts, by weight, of a non-biodegradable, tacky, polymeric binding agent, from 12 to 25 parts, by weight, of an inert reinforcing filler and a coating on at least the intended skin contacting face of the dressing of a non-biodegradable, water-activated adhesive/thickener, the composition having an aqueous swell value of from 5 to 40% and a cold flow value of from 50 to 90%. It may be used for ostomy applications. This adhesive is said to obviate certain disadvantages of known materials in that it adheres satisfactorily to moist surfaces, it absorbs moisture and maintains its adhesion and is physiologically acceptable.

Kao Corporation in Japanese Patent Application 1982-058535 disclosed a pressure sensitive adhesive sheet comprising a base fabric which has stretching properties in 1 or 2 directions, that is, a degree of 20% stretching at 1.50 g/cm load, and an adhesive layer. This adhesive layer comprises (a) 3.25 wt. % water soluble polyol of hexylene glycol, polyethylene glycol of less than 1000 mol. wt., glycerine or sorbitol, (b) 1.25 wt. % water soluble or water swelling polymer and (c) remaining wt. % of adhesive agent(s) (where sum of (a) +(b) must be more than 6 wt. %.

E. R. Squibb & Sons, Inc. in European Patent (EP) 307187 disclosed a dressing comprising a flexible backing member and a pressure sensitive adhesive layer. The adhesive layer comprises one or more polyisobutylenes, elastomers, and one or more moisture absorbing, moisture transmitting, water soluble and/or water swellable agents. According to the teaching in EP 307187, a dispersion of an active ingredient in a medium compatible with the adhesive layer is laminated to the skin contacting surface.

The same Applicant in EP 297769 taught that a pressure sensitive acrylic adhesive mass is made hydrophillic by blending one or more water/moisture absorbing, water/moisture transmitting substances into the acrylic mass. The resulting adhesive is particularly suited for medical use such as in bandage and wound dressing type products. The disclosed production method uses solvent and can make pads of thickness typically up to 0.1 mm compared with typically in excess of 0.5 mm for the preferred products according to the present invention. Also, the additives would be leachable.

Nitto Denko Corporation in EP 528191 disclose a dressing comprising a backing and an adhesive layer, wherein said backing is moisture-permeable and said adhesive layer comprises an adhesive composition comprising a rubber-based adhesive, a polymer having a water-absorbing property and/or a water-swelling property and a metal oxide and/or a metal salt, said polymer having the water-absorbing property and/or the water-swelling property being a polymer containing is a functional group having an ability to form a salt and/or to co-ordinate. The present invention does not rely on a metal oxide or a metal salt for acceptable operation.

LTS Lohmann Therapie-Systeme in PCT Application WO95/31188 disclose a system for delivering substances contained in hot-melt type pressure-sensitive adhesives with a uniform or irregular distribution of the substances characterised in that the hot-melt type pressure-sensitive adhesive is hydrophillic and contains at least one water-soluble or at least water-swellable polymer, at least one water-soluble, hot-melt type adhesive resin and the substance to be delivered.

In WO95/31514 of SULC there is disclosed a composite pressure sensitive adhesive particularly suitable for temporary gluing medical and cosmetic means to the body surface from which it can be easily removed by liquid water or by innocuous diluted aqueous solutions. Such a product is described as a gelled mixture of a water swellable, water insoluble polymer, soluble in polar water-miscible solvents boiling at atmospheric pressure at temperatures higher than 100° C. as well as their mixtures with minor amounts of water; a hydrophillic water swellable polymer, insoluble in water as well as in polar water-miscible solvents boiling at atmospheric pressure at temperatures higher than 100° C.; and a polar water-miscible innocuous solvent boiling at atmospheric pressure at temperatures higher than 100° C., if desired mixed with a minor amount of water.

Reference is also made to GB-A-2046764 and U.S. Pat. No. 4,768,503 which describe a polymeric composition adhesive for use in skin contact applications. The composition uses a chemically cross-linked hydrophilic polymer and a support matrix such as a high molecular weight hydrophobic polymer. The hydrophilic polymer is water-swellable, but water insoluble. The composition preferably includes a tackifier which may be provided by a low molecular weight fraction of a hydrophobic matrix, or by a distinct adhesive component such as gum or a low molecular weight polymer. The composition is said to be especially suitable for post-surgical drainage applications.

SUMMARY OF THE INVENTION

In one aspect, an aim of the present invention is to devise a formulation in which a pressure sensitive adhesive retains a high proportion of its strength when exposed to an excess of water or water vapour, such as that which emanates from the skin surface which applies to the whole adhesive in contact with the skin.

A perceived advantage is that the adhesive will retain its integrity and its tensile strength i.e. will not be eroded, and thus when the patient removes the adhesive from the skin it will be removed in a coherent layer and will not leave residues on the skin surface.

It is preferably desired that the adhesive should retain a high proportion of its strength when exposed to an excess of water when the edge of the adhesive is exposed when for example bathing, showering or swimming; or when the edge of the adhesive is exposed to contact with body fluids emanating from stoma.

In these instances there will be copious quantities of water available, of which a proportion can be absorbed by the adhesive on the exposed edges. A water soluble material and a hydrocolloid to a lesser extent may be eroded leaving the pressure sensitive adhesive matrix in a stringy type situation or significantly reduced in tensile strength. Thus when the adhesive is removed there is locally on the edges a weak material which on removal from the skin surface may leave residues. In the latter case the body fluids are water based and contact occurs over the period of wear of the adhesive which may be typically 7 days.

The most important function of the adhesive is to adhere to the skin. The skin may be damp when the adhesive is applied and also the skin will release water from its surface throughout the presence of the adhesive on the skin. Therefore in order that the pressure sensitive adhesive functions most effectively then it is desired that the adhesive is capable of absorbing a small amount of liquid water initially and in the vapour state the whole time the adhesive is in position on the skin.

A further problem addressed by another aspect of the invention is that, as the adhesive absorbs water, it tends to expand in all directions. FIG. 1 illustrates a typically shaped adhesive pad 10 for attaching an ostomy coupling to the peristomal area of the body. The pad has central aperture 12 which surrounds the stoma to allow body waste to pass therethrough. As illustrated schematically in FIG. 2, the absorption of water will cause the pad to swell outwardly as depicted by the shape 10a (compared to its original shape 10), but the expansion of the material will also tend to reduce the stoma aperture 12a (compared to its original size 12). This will hinder the passage of the body waste into the ostomy bag and, in extreme cases, can cause a blockage at the aperture.

A further problem addressed by the invention is that some conventional skin adhesives can suffer from cold flow (creep) during storage. For example, in some conventional adhesive ostomy pads, the adhesive may tend to ooze at the pad edges during storage. This is caused by the adhesive material creeping under gravity even in its absence of external physical loads. One option tried in the art is to crosslink the polymer chains in the adhesive. Although this can reduce cold flow creep, crosslinking can reduce the adhesive strength by reducing the number of available adhesive sites in the polymer chains.

According to one aspect of the present invention, there is provided an adhesive composition or structure, for use in skin application, e.g. wound care, or for attaching devices to collect body waste to the wearer, said composition comprising (a) a polymer or mixture of polymers which act as a pressure-sensitive adhesive present in an amount 20–60 parts by weight of the adhesive composition; and (b) a water-swellable polymer which will absorb from 50 to 500 grams of water per 100 grams of water-swellable polymer, the latter being present in an amount 20–80 parts by weight of the adhesive composition (or more preferably 40–80 parts by weight).

According to an alternative version of the invention, an adhesive composition is provided which is as defined in the preceding paragraph except that there is additionally present up to 30 parts by weight (of the adhesive composition) of a water-soluble polymer. The main purposes of this component of the adhesive is to assist in the absorption of any residual water on the skin surface at the time of application of the adhesive, and to ensure there is an adequate bond between the skin and the pressure sensitive component of the adhesive. The water soluble polymer which when dissolved in water desirably has adhesive properties thereby provides the desired initial tack.

Thus to obtain the initial adhesion a proportion of a water soluble component is desired and to meet the long term requirements of water vapour (perspiration) then a water swellable polymer is used. The combination of these two compounds in the adhesive matrix enable the water to be transported through the adhesive and slowly released through the protective covering on the adhesive on the non-skin side of the adhesive.

If this process does not occur, then if the ostomate transpires a large amount of water vapour, there will be formed a liquid water layer on the skins surface and the adhesion strength will be significantly reduced, and can lead to failure of the adhesive, i.e. pouch falls off.

The use of these proportions of water-swellable polymer provides significant advantages. When a water-swellable polymer absorbs water, it maintains a degree of physical strength and will only absorb up to a certain amount of water. This contrasts with a water soluble material, which will absorb water and eventually go into solution, and possesses no physical strength or even physical integrity. For example contact lenses have strength, gelatine in solution has none. This has particular relevance in the case of pressure sensitive adhesive compositions used to attach appliances or devices to the human skin.

According to a preferred aspect of the invention, an adhesive composition may comprise:

|  | Range | Preferred |
| --- | --- | --- |
| Adhesive Polymer(s) | 20–60 | 40 |
| Water Swellable Polymer | 20–80 | 40–80 (typically 40) |
| Water Soluble Polymer | 0–30 | 20 |

Figures are in percent by weight.

A presently-preferred material for the water-swellable polymer is the product of radiation cured polymerisation from a monomer mixture of methyl methacrylic acid, n-vinyl-2-pyrrolidone and styrene. Other examples of suitable polymers include those using acrylic acid and its co-polymers, and vinyl pyrrolidone. Also usable are fibres coated with a superabsorbent polymer, such as sodium polyacrylate coatings on acrylic fibres.

Preferably, the adhesive polymers (40%) comprise 10% by weight of one or more polymers of relatively high molecular weight, and 30% by weight of one or more polymers of relatively low molecular weight.

A suitable material for the adhesive polymer mentioned above may be any of the following:—polyisobutylene, polyurethane, natural rubber, polyisoprene, etc.

A suitable material for the water-soluble polymer referred to above may be either or both of the following:—carboxymethyl cellulose and pectin. These materials are strongly preferred because they have a greater rate of development of wet-tack with small quantities of water than other materials such as Karaya (as used for example in GB-A-2046764 and U.S. Pat. No. 4,768,503). It will be appreciated that the amount of water soluble material employed in the adhesive composition of the invention can be significantly less than in other conventional adhesives without a water swellable polymer. In some circumstances, this might detract from the wet-tack of the composition, since the water soluble material provides the initial tackiness. Therefore, it is important that the rate of development of wet-tack of the limited amount of water-soluble material be fast, to provide a good initial wet-tack until the pressure sensitive adhesive has time to achieve an optimum adhesive strength.

In a preferred form, the composition comprises approximately equal quantities of pectin and carboxymethyl cellulose (for example, 10% wt of each material).

It will be understood that adhesives used for skin applications such as woundcare and ostomy appliances, are often formulated to absorb water (or perspiration) arising from the skin surface. This absorption results in the adhesive swelling.

These adhesives also absorb liquid water as a result of, for example, bathing and contact with body excretions. This contact which occurs with liquid water is essentially on the edge of the adhesive. The direction of swelling of the absorbing component(s) of the adhesive will be primarily in the direction away from the adhesive bulk, with a smaller proportion in a direction generally perpendicular to the surface of the adhesive contacting the skin.

The effect of this expansion is to cause the adhesive to protrude outside the original confining area, making it prone to further damage by erosion and/or leaching, and/or by adhesion to other surfaces. The work resulting in the present invention has shown that by using, in the composition, a major proportion of a absorbent material which is water swellable, but not water soluble, the leaching effect can be significantly reduced. Further improvements to reduce the level of erosion have been achieved by using water-swellable absorbent material having a particle size of less than 200 microns and preferably less than 100 microns, and having an absorption of water of less than 5 grams per gram and preferably less than 3 grams per gram but greater than 0.5 grams per gram.

In a further aspect, the invention provides an adhesive composition or structure for use in skin application, comprising (a) a water-swellable polymer; and (b) a mixture of polymers which act as a pressure sensitive adhesive, the mixture including one or more first polymers of relatively low molecular weight, and one or more second polymers of relatively high molecular weight compared to the first polymers.

By including both relatively low and high molecular weight polymers in the mixture, cold flow problems can be minimised while at the same time, the adhesive is sufficiently miscible at suitable temperatures during production.

The high molecular weight polymer has relatively long polymer chains, and such chains are difficult to move past each other, which then reduces cold flow of the material. However, it has been appreciated during the development of this invention that a pressure sensitive adhesive consisting only of long polymer chains would be difficult to mix during production. The inclusion of low molecular weight polymers (having relatively short polymer chains) can reduce this problem by the shorter chains getting between the longer chains, and reducing the anchoring effect of the longer chains. In other words, the long polymer chains can reduce cold flow (creep) effects when the adhesive is under only thermal load, and the shorter polymer chains act as a "lubricant" to improve miscibility under sheer loads during mixing at elevated production temperatures.

In a yet further aspect, the invention provides an adhesive composition or structure for use in skin application, for example, drug delivery, wound care, or for attaching devices to collect body waste to a wearer, said composition comprising (a) a polymer or mixture of polymers which act as a pressure-sensitive adhesive; and (b) fibres coated with a water-swellable polymer and having a characteristic such that the fibres prevent substantial expansion of the water-swellable material in is an axial direction of the fibres.

Such a composition can introduce a unique anisotropic or directional swelling property not hitherto appreciated. In particular, by suitably arranging the fibres, the adhesive can be arranged to swell in a first predetermined direction in preference to a second direction. For example, if the fibres are arranged to lie in, or parallel to, an x-y plane (i.e. very few fibres extending in a z direction), then the adhesive will tend to swell in the z direction and not in the x and y directions;

the fibres extending in the x and y directions tend to prevent expansion in this plane.

The above principles can be exploited in an adhesive pad having an aperture therein. By arranging for the pad to swell in a direction parallel to the axis of the aperture in preference to transverse directions, any tendency for the swelling material to block the aperture can be avoided, or at least significantly reduced.

Although the individual aspects of the invention can be used independently of each other excellent results can be achieved by combining together two or more of the aspects.

BRIEF DESCRIPTION OF THE DRAWINGS

Embodiments of the invention are now described with reference to the accompanying further drawings, in which.

According to a preferred embodiment of the invention, an adhesive composition for use in skin application comprises (a) a polymer or mixture of polymers which act as a pressure-sensitive adhesive present in an amount 30–50 parts by weight; and (b) a water swellable polymer which will absorb from 50 to 500 grams of pure water per 100 grams of water-swellable polymer, the latter being present in an amount 30–70 parts by weight of the adhesive composition (or more preferably 50–70 parts by weight).

A particularly preferred composition, with the quantities specified as % wt, is as follows:
(a) 40% superabsorbent hydrophilic polymer (Biogel WA3S obtainable from I. H. Polymeric Products, Gravesend, U.K.);
(b) 30% polyisobutylene having a molecular weight of about 2000 (Hyvis 2000 obtainable from British Petroleum, Grangemouth, U.K.);
(c) 10% polyisobutylene having a molecular weight of about 14000 (Vistanex MML140 obtainable from Exxon, Notre Dame de Gravenchon, France);
(d) 10% pectin (Genu Pectin (Citrus) obtainable from Hercules of Copenhagen, Denmark); and
(e) 10% sodium carboxy methyl cellulose (Blanose obtainable from Aqualon, Malmaison, France).

In the practice of this invention it is preferred to use a sheet of adhesive having a thickness of 0.2 mm to 2.0 mm, and to one side of the adhesive may be a release film such as a silicone coated polyester or a release paper such as a silicone coated paper. On the other side may be a thin pliable water insoluble film which may be bonded directly to the pouch or to a flange system. This film may be a plain film, an embossed film or a microporous film. The film is preferably water permeable so as not to interfere with the advantageous absorption transpiration properties of the composition.

According to a different but advantageous version of the invention, one may use the water-swellable polymer in the adhesive composition by placing it on a coated fibre; with this arrangement the fibre coated with polymer will not expand significantly in a longitudinal direction but will expand radially of the fibre.

Figure 1:
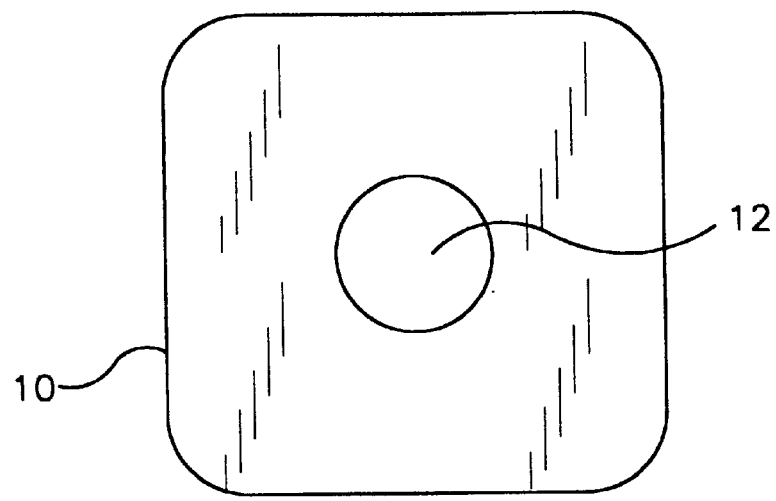
FIGS. 1 and 2 are schematics of prior art skin pads.
Figure 2:
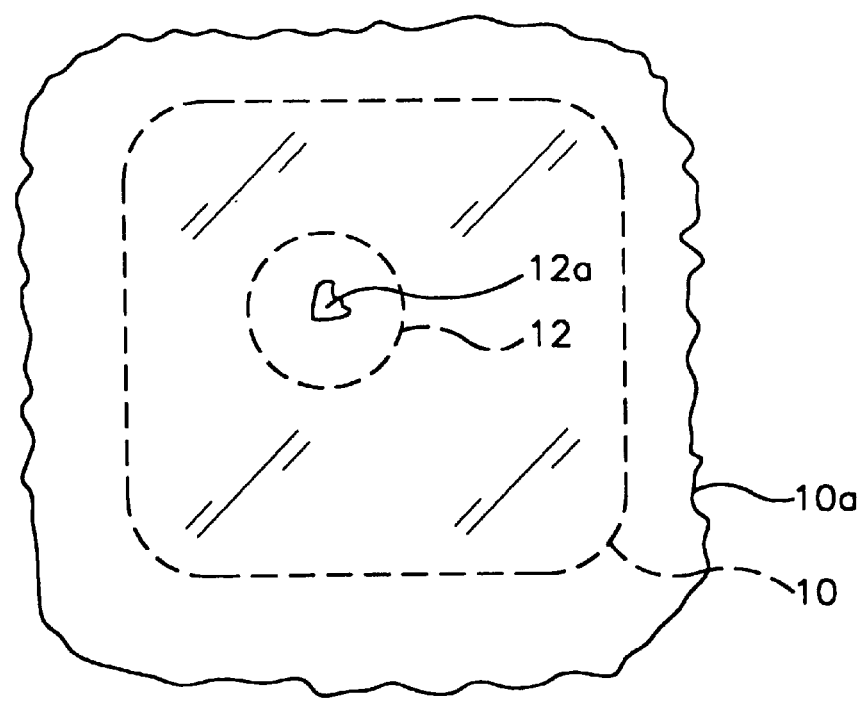
Figure 3:
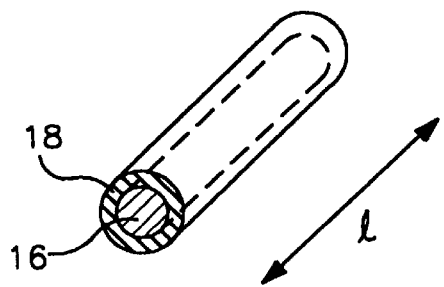
FIGS. 3 and 4 are schematic illustrations of a coated fibre before and after absorption of water.
Figure 4:
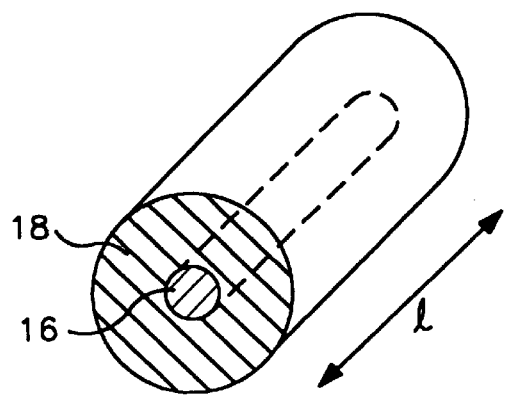

This effect is illustrated schematically in FIGS. 3 and 4. The fibre core or filament 16 may, for example, be of acrylic, and the coating 18 may, for example, be of sodium polyacrylate. Coated fibres of such materials are obtainable from Technical Absorbents Ltd., of Grimsby, U.K., under the trade name "Oasis". It is emphasised that FIGS. 3 and 4 are merely schematic and are not to scale.

The fibre core is neither water soluble nor water swellable, and its dimensions do not change substantially in the presence of water. The water-swellable coating is bound to the fibre and so cannot expand or swell substantially in the longitudinal (axial) direction. Therefore, the only direction in which the water-swellable polymer can expand is radially of the fibre.

In use, the coated fibres may be laid in contact with the remainder of the adhesive composition to form a composite adhesive structure or composition. However, it is preferred that the coated fibres be mixed into the adhesive composition to form a generally homogeneous mixture.

If it is desired to exploit the directional expansion properties provided by the coated fibres (to promote expansion in a particular direction), then it is necessary to align or otherwise arrange the fibres relative to the directions in which expansion is to be controlled. Since a large number of fibres extending in a particular direction will tend to prevent expansion in that direction, relatively few fibres should be arranged to extend in directions in which substantial expansion is to be permitted.

Figure 5:
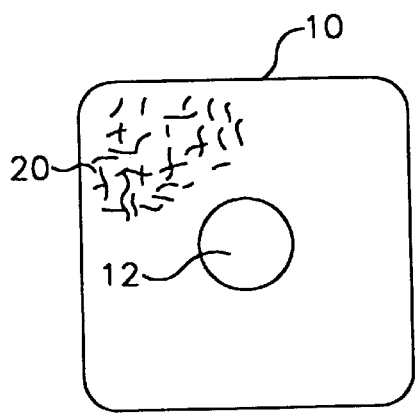
FIG. 5 is a schematic plan view of an adhesive pad with coated fibres.
Figure 6:
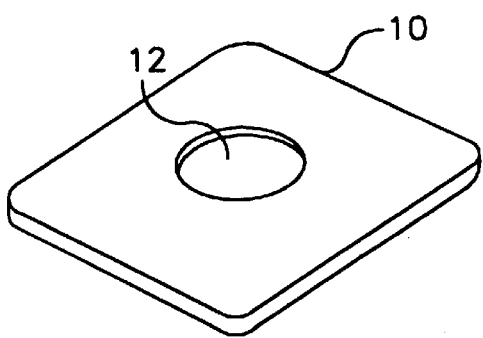
FIGS. 6 and 7 are schematic perspective drawings illustrating the pad of FIG. 5 before and after absorption of water.
Figure 7:
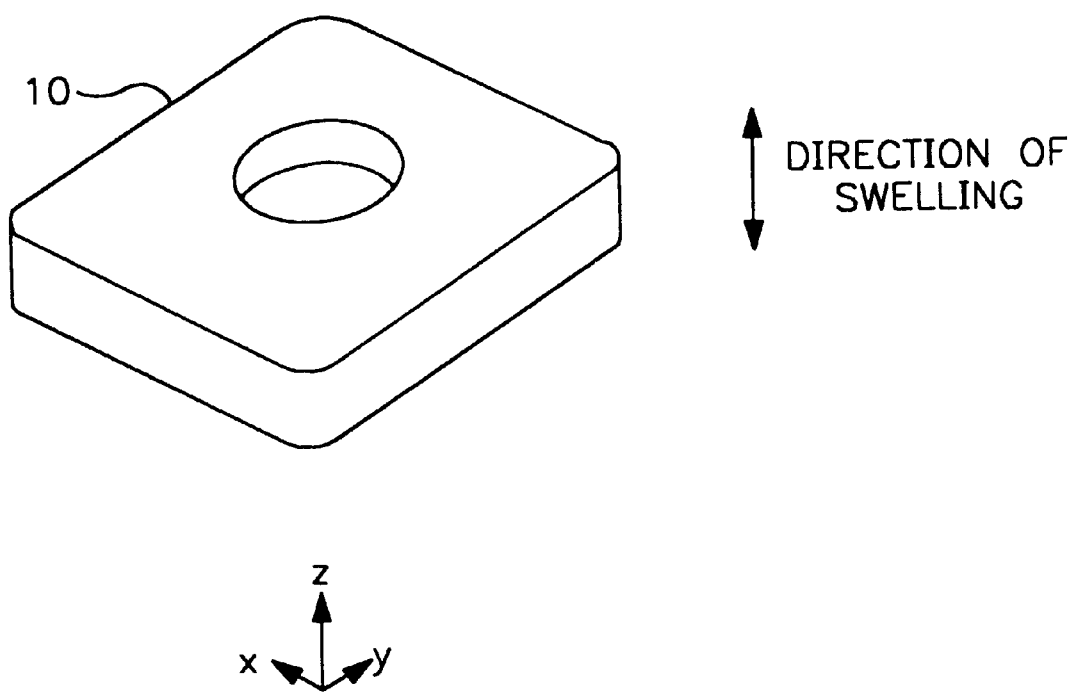

An adhesive pad for attaching an ostomy bag to the peristomal area of the wearer, and including coated fibres, is illustrated in FIGS. 5 to 7. In this embodiment, the pad is relatively thin in the z direction, and the fibres (indicated schematically by the lines 20 in FIG. 5) are thus generally confined to extend in the x-y plane. As illustrated in FIG. 7, when the water-swellable material expands as it absorbs water, the expansion is limited to be predominantly in the z direction, with very little or no expansion occurring in the x and y directions. Thus this design can avoid the problem in the prior art that the adhesive material may expand across the stoma aperture causing a blockage. Moreover, the adhesive composition can reduce cold flow (creep) effects, and avoid (or at least reduce) the problem of the adhesive oozing at the pad edges.

The adhesive structure can be formed by any suitable shaping process. For example, a thin pad can be formed by extrusion and/or pressing of the adhesive material.

Figure 8:
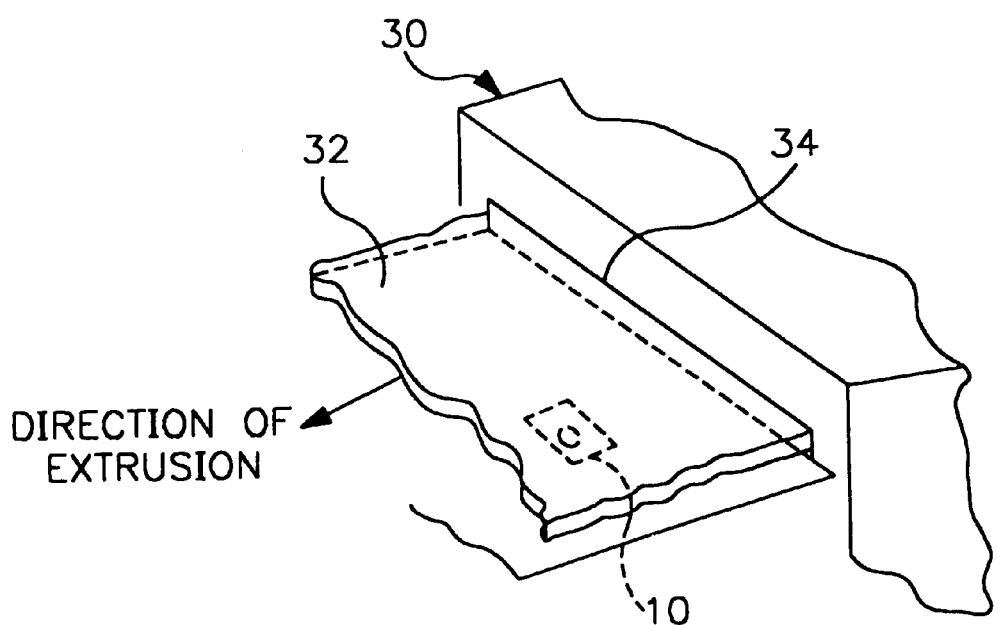
FIG. 8 illustrates schematically an example extruder.

FIG. 8 illustrates schematically an example extruder 30. The adhesive material 32 is forced through a narrow slot 34, to form a thin extruded sheet or web. Typically, the slot will be a few millimeters in height to define the sheet thickness. If desired, the sheet thickness can be further reduced by advancing the sheet between pressure rollers (not shown) known per se. The slot will typically be much wider than it is high, and may have a width of about a meter or more.

The extruding of the material 32 through the narrow slot 34 will tend to orientate the water-swellable polymer-coated fibres in the (x-y) plane of the sheet. It is expected that the fibres may be aligned predominantly in the direction of extrusion (x direction), but that tangling of the fibres may also occur so that at least some of the fibres will have components in the transverse (y) direction.

The individual adhesive pads may be formed by stamping the pads (an example of which is shown in FIG. 8 in phantom) from the extruded sheet in a conventional manner.

Although the invention has been described in relation to an ostomy application, the invention is not limited to this field. The invention may be used generally for attachment to a wearer's skin; particular applications include woundcare and, optionally, drug delivery.

It will be appreciated that many modifications may be made within the scope and/or principles of the invention. Although features believed to be of particular importance have been set out in the attached claims, the applicant claims protection for any novel feature or combination of features disclosed herein and/or illustrated in the attached drawings, irrespective of whether emphasis has been placed thereon.

We claim:

1. An adhesive composition for use in skin applications comprising:

a) at least one adhesive polymer selected from the group consisting of polyisobutylene, polyurethane, natural rubber, chlorobutyl rubber, radiation curable ethylene—propylene elastomer, a silane grafted moisture curable material and polyisoprene, comprising 20–60 parts by weight of the composition;

b) a water-swellable polymer selected from the group consisting of i) a mixture of methacrylic acid, n-vinyl 1–2 pyrrolidone and styrene, ii) a copolymer of vinylpyrrolidone and acrylic acid, iii) a copolymer of methacrylic acid and polyvinyl pyrrolidone, iv) sodium polyacrylate coating in acrylic fibers, v) a cross-linked polyacrylanide, comprising 20–80 parts by weight of the composition; and c) at least one water-soluble polymer selected from the group consisting of pectin and carboyxmethylcellulose, comprising 0–30 parts by weight of the composition, wherein when said composition is exposed to 36° C. and 100% relative humidity for eight days it absorbs at least 25% by weight of water and retains at least 50% of its tensile force.

2. The adhesive composition of claim 1 wherein said at least one water-swellable polymer comprises 40–80 parts by weight of the composition.

3. The adhesive composition of claim 1 wherein said water-soluble polymer comprises 20 parts by weight of the composition.

4. The adhesive composition according to claim 3 wherein said water-soluble polymer is one half pectin and one half carboxymethylcellulose.

5. The adhesive composition of claim 1 wherein said adhesive polymer includes at least one first polymer of low molecular weight and at least one second polymer of relatively high molecular weight compared to said first polymer.

6. The adhesive composition of claim 1 wherein said water-swellable polymer is a sodium polyacrylate coating on acrylic fibers, and said fibers longitudinally extend substantially in one direction.

7. The adhesive composition of claim 1 wherein said composition is formed into a shape of a pad.

* * * * *